United States Patent [19]
Sheppard et al.

[11] 4,218,370
[45] Aug. 19, 1980

[54] AZO MONOMER USEFUL IN POLYMERIZATION SYSTEMS

[75] Inventors: Chester S. Sheppard, Kenmore; Ronald E. MacLeay, Williamsville, both of N.Y.

[73] Assignee: Pennwalt Corporation, Philadelphia, Pa.

[21] Appl. No.: 38,992

[22] Filed: May 14, 1979

[51] Int. Cl.² .................... C07C 107/02; C08J 9/00
[52] U.S. Cl. .................... 260/192; 260/152; 260/156; 260/164; 260/925; 526/218; 526/219; 526/344
[58] Field of Search ............... 260/152, 156, 164, 192

[56] References Cited
U.S. PATENT DOCUMENTS

| | | | |
|---|---|---|---|
| 3,993,609 | 11/1976 | Kamens et al. | 260/2.5 R |
| 4,007,165 | 2/1977 | MacLeay et al. | 260/192 |

*Primary Examiner*—John Doll
*Attorney, Agent, or Firm*—David Edwards

[57] ABSTRACT

An unsymmetrical azo monomer contains t-alkyl, t-cycloalkyl, or t-aralkyl moiety and one polymerizable double bond. This compound is useful in polymerization and crosslinking systems.

6 Claims, No Drawings

AZO MONOMER USEFUL IN POLYMERIZATION SYSTEMS

BACKGROUND OF THE INVENTION

The present invention relates to an azo monomer and more particularly to a tertiary alkyl, tertiary cycloalkyl or tertiary aralkyl azoalkane which contains only one polymerizable double bond.

In the prior art, unsymmetrical t-alkyl azo compounds are taught in U.S. Pat. Nos. 3,993,609, 4,028,344 and 4,007,165. Although some of these patents teach broadly that double bonds can be present, none of them, however, teach that such double bonds, if present, can be copolymerized. The azo monomers of the present invention do not come within the scope of this prior art.

German Pat. No. 1,055,240 teaches symmetrical polymerizable azo compounds which contain a polymerizable double bond on each side of the azo function. The compound of the present invention does not come within the scope of this prior art because the compound of the present invention is an unsymmetrical azo compound containing only one polymerizable double bond per molecule that has some unobvious advantages over the symmetrical compounds of the prior art. Since the symmetrical azo compounds of the German patent have two double bonds, they can act as crosslinking agents by copolymerizing with two different growing chains. This leads to high molecular weight crosslinked polymers which are very difficult to work with as was experienced in the copolymerization of vinyl acetate with diallyl 4,4'-azobis(4-cyanovalerate) prepared from 4,4'-azobis(4-cyanovaleroyl chloride) and allyl alcohol. This was not a problem when methyl methacrylate was copolymerized with 2-(methacryloxy)-ethyl 4-t-butylazo-4-cyanovalerate (called MEBC) in Example 4, infra. This German patent, only teaches one method of preparing copolymers from their polymerizable azo compounds, that is, the copolymer of the azo compound and a vinyl monomer is prepared under conditions such that the azo group is retained in the copolymer.

R. Kerber, O. Nuyken and R. Steinhausen, Makromol. Chem. 177, pp. 1357–1371, (1976) synthesized unsymmetrical aryl-azo monomers. These aryl-azo monomers were copolymerized with styrene to form azo containing polystyrene copolymers that were grafted with acrylonitrile to form polystyrene-polyacrylonitrile graft copolymers. The aryl-azo monomers of Kerber, et al. are different from those of the present invention since the azo monomers in the present invention are tertiary-alkyl, tertiary-cycloalkyl or tertiary-aralkyl azo compounds. This is a significant difference since aryl-azo groups are the highly chromophoric functions of the classical azo dyes while alkyl-azo groups are not. Thus, Kerber's azo compounds are necessarily highly colored and can impart undesirable color bodies into polymers whereas the azo monomers of the present invention do not.

Kerber's aryl-azo compounds all contain two alphacyano moities which limits their temperature activity and presents toxicity problems both in the azo itself and its decomposition fragments while the alkyl-azo monomers of the present invention do not have these drawbacks.

SUMMARY OF THE INVENTION

The present invention is directed to a compound of the formula

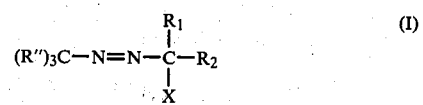

wherein:

(a) R''s are independently selected from alkyl of 1 to 8 carbons, aralkyl of 7 to 12 carbons, or aryl of 6 to 14 carbons, with the proviso that only one R'' may be aryl, the R''s can also be joined to form a cyclo, bicyclo or tricyclo of 3 to 12 carbons;

(b) $R_1$ and $R_2$ are independently selected from alkyl of 1 to 8 carbons, cycloalkyl of 3 to 12 carbons, aralkyl of 7 to 12 carbons, or a ring substituted cycloalkyl of 5 or 6 carbons wherein the ring substituent is one or more of oxygen, nitrogen or sulfur, $R_1$ and $R_2$ can be joined to form an alkylene diradical of 3 to 11 carbons, $R_1$ can also be an aryl of 6 to 14 carbons;

(c) X is selected from

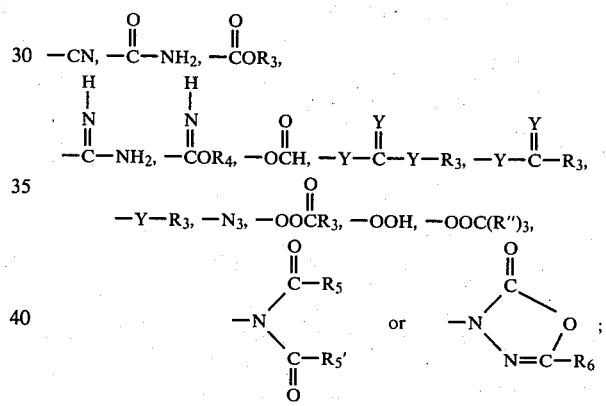

(d) Y is selected from oxygen or sulfur;
(e) $R_3$ is selected from alkyl of 1 to 8 carbons, cycloalkyl of 3 to 12 carbons or aryl of 6 to 14 carbons;
(f) $R_4$ is selected from alkyl of 1 to 6 carbons;
(g) $R_5$ and $R_5'$ are independently selected from alkyl of 1 to 8 carbons or aryl of 6 to 14 carbons, $R_5$ and $R_5'$ can be joined to form an alkylene diradical of 1 to 8 carbons or an arylene diradical of 6 to 14 carbons;
(h) $R_6$ is selected from hydrogen, alkyl of 1 to 8 carbons, cycloalkyl of 3 to 12 carbons or aryl of 6 to 14 carbons;
(i) one of $R_1$, $R_2$, $R_3$, $R_4$, $R_5$, $R_6$ or R'' must be substituted with

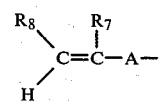

(j) $R_7$ is selected from hydrogen, alkyl of 1 to 6 carbons or Cl—;
(k) $R_8$ is selected from hydrogen or

(l) $R_9$ is selected from H or alkyl of 1 to 6 carbons;
(m) when $R_8$ is hydrogen, A is selected from

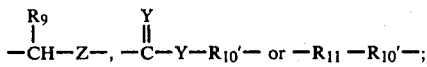

(n) when $R_7$ and $R_8$ are both hydrogen, A is selected from

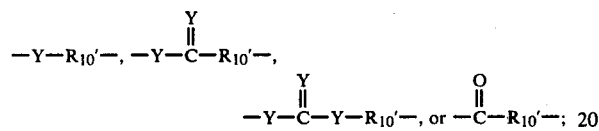

(o) when $R_8$ is

$R_7$ is hydrogen and A is

(p) Z is selected from

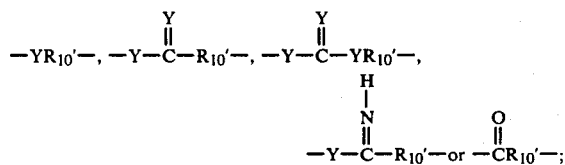

(q) $R'_{10}$ is selected from a covalent bond or $-R_{10}D-$;
(r) $R_{10}$ is selected from alkylene of 1 to 8 carbons;
(s) D is selected from

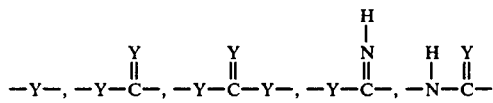

or covalent bond; and
(t) $R_{11}$ is selected from aryl of 6 to 14 carbons, pyridine, carbazole, pyrrolidone, piperidone or caprolactam.

This invention is also directed to the use of the above mentioned compound in improved free radical polymerization systems such as:

(1) Formation of azo-containing polymers by copolymerization of the azo-monomers with vinyl monomer(s) under conditions such that the azo group is retained, usually in the presence of an initiator active at lower temperatures than the azo.

(2) Formation of monomer-terminated polymers by polymerization of vinyl monomers using the azo-monomer as the initiator wherein the vinyl monomer has a higher reactivity than the monomer on the azo compound.

(3) Formation of graft copolymers by using an azo-containing polymer from (1) above as the initiator in the polymerization with a vinyl monomer(s).

(4) Formation of graft copolymer by using the monomer-terminated polymer from (2) above with a vinyl monomer having a suitable reactivity ratio in the presence of a free radical initiator.

(5) Formation of an azo-containing polymer by the homopolymerization of the azo-monomer in the presence of a lower temperature active free radical initiator.

(6) Improved polymerizations of vinyl monomers using the azo-homopolymer from (5) as the free radical initiator.

(7) Obtaining faster polymerization rates without sacrifice in polymer molecular weight by using the azo-monomer as the sole or co-initiator in the (co)-polymerization of vinyl monomers.

(8) Obtaining polymers of higher molecular weight by using the azo-monomer as the sole or co-initiator in the (co)polymerizations of vinyl monomers at equivalent or faster rates.

(9) Curing resins curable by free radical initiators using the azo-monomer as the initiator.

(10) Foaming and curing resins by using the azo-monomer as a blowing agent.

(11) Foaming and curing resins by using an azo-polymer (e.g. from (1) above) as the blowing agent.

(12) Formation of crosslinked polymers by polymerizing monofunctional vinyl monomers using the structure I azo-monomers as a (co)initiator without employing crosslinking co-agents.

DETAILED DESCRIPTION OF THE INVENTION

For purposes of this invention, alkyl radicals include such moieties as methyl, ethyl, isopropyl, propyl, butyl, isobutyl, tertiary butyl, secondary butyl, pentyl, hexyl, heptyl, and octyl. Aralkyl radicals include benzyl, phenethyl, cumyl, p-isopropylbenzyl, 3,5-dimethylbenzyl, p-t-butylphenethyl, and p-t-amylbenzyl. The aryl radical includes phenyl, 2-,3-, or 4-methylphenyl, xylyl, p-isopropyl-phenyl, p-t-butylphenyl, naphthyl, phenanthryl, and bi-phenylyl. The cyclo, bicyclo and tricyclo radicals include cyclopropyl, cyclopentyl, cyclohexyl, cyclooctyl, cyclodecyl, cyclododecyl, 3,3,5-trimethylcyclohexyl, 4-methylcyclohexyl, bornyl, isobornyl, fenchyl, norbornyl, and adamantyl.

The heterocyclic (or ring substituted) radicals include 2-,3-, or 4-pyridyl, 2- or 3-thienyl, 2-,3-, or 4-pyranyl, 2- or 3-furyl, and 2- or 3-tetrahydrofuryl. The alkylene diradicals include methylene, ethylene, propylene, tetramethylene, octamethylene, undecamethylene, and 1,3,3-trimethyltetramethylene. Arylene diradicals include phenylene, naphthylene, phenanthrylene, biphenylene, and methylphenylene.

Suitable polymerizable double bonds that may be built into the structure (I) include such groups as: allyl and methallyl ether and thioether groups; allyl and methallyl ester, and thioester groups; allyl and methallyl carbonate and thiocarbonate groups; allyl and methallyl iminoester and thioiminoester groups; or allyl and methallyl ketone groups; acrylate and methacrylate ester and thioester groups; vinyl aromatic groups such as styrene, alpha-methylstyrene, chlorostyrene, vinylnaphthalene, vinylanthracene, and vinyl toluene; vinyl heterocyclics such as vinylpyridine, vinylpyrrolidone, and vinyl carbazole; vinyl ether and thioether groups; vinyl ester and thioester groups; vinyl carbonate and thiocarbonate groups; vinyl ketones; maleate or fumarate ester groups; and maleic acid or fumaric acid groups.

In one method of preparing graft copolymers using the structure (I) compound, a copolymer of styrene and methyl methacrylate is prepared by copolymerizing methyl methacrylate and 2-(methacryloxy)ethyl 4-t-butylazo-4-cyano-valerate (called MEBC). The resultant azo-containing copolymer is then heated to 80° C. in the presence of styrene to form the styrene-methyl methacrylate copolymer (see Examples 4 and 5). (see also Examples 11, 12, 13, 20, 21 and 24 for preparing azo-containing polymers and Examples 16, 22 and 23 for preparing graft copolymers).

In another method of preparing graft copolymers using the structure (I) compound, a copolymer of styrene and vinyl acetate is prepared by polymerizing styrene with allyl 4-t-butylazo-4-cyanovalerate (from Example 1) and then copolymerizing the resultant styrene polymer containing the allyl end group with vinyl acetate. The allyl group is much less reactive than the double bond in styrene and consequently does not copolymerize very well with styrene. On the other hand, the allyl group and the vinyl group in vinyl acetate have similar reactivities and the styrene polymer having the allyl end group copolymerizes easily with vinyl acetate. (see Example 2).

The graft copolymers which are formed from the structure (I) compound and the vinyl monomers using one of the above techniques are useful in a variety of applications such as compatabilizing agents for mixtures of the homopolymers, impact modifiers, adhesives and other polymer property modifications. The usefulness of graft copolymers is well known (see e.g. "Block and Graft Copolymers" by R. J. Ceresa, Washington, Butterworths, 1962 and "Block and Graft Polymers" by W. J. Burlant and A. S. Hoffman, New York, Reinhold, 1961).

In using the structure (I) compound to prepare an azo-copolymer, it is advantageous to choose one wherein the azo group is stable under the reaction conditions and the double bond of the structure (I) compound has a favorable reactivity ratio with the monomer to which it is to be copolymerized (see J. Brandrup and E. H. Immergut, Polymer Handbook, Interscience Publishers, New York, 1966). The monomer reactivity ratios $r_1$ and $r_2$, for any monomer pair are the ratios of the rate constants of different propagation reactions as defined:

| $M_1' + M_1 \rightarrow M_1M_1'$ | Rate Constant $k_{11}$ |
| $M_1' + M_2 \rightarrow M_1M_2'$ | Rate constant $k_{12}$ |
| $M_2' + M_2 \rightarrow M_2M_2'$ | Rate constant $k_{22}$ |
| $M_2' + M_1 \rightarrow M_2M_1'$ | Rate constant $k_{21}$ |
| $r_1 = k_{11}/k_{12}$ | |
| $r_2 = k_{22}/k_{21}$ | |

If the reactivity ratio of the vinyl group of the azo initiator is similar to that of the vinyl monomer or larger, the copolymerization should incorporate a considerable amount of the azo initiator into the copolymer. If the reactivity ratio of the vinyl group of the azo initiator is smaller than that of the vinyl monomer, a smaller amount of the azo initiator will be incorporated into the copolymer. Therefore, it is very important to consider the reactivity ratios when considering which structure (I) compound and the amount of the structure (I) compound to be used in the copolymerization.

The structure (I) compounds can be copolymerized with vinyl monomers such as olefins, such as ethylene, propylene, styrene, alphamethylstyrene, chlorostyrene, vinyltoluene, vinylbenzyl chloride, vinylpyridine and divinylbenzene: diolefins, such as 1,3-butadiene, isoprene and chloroprene; vinyl esters, such as vinyl acetate, vinyl propionate, vinyl laurate, vinyl benzoate and divinyl carbonate, unsaturated nitriles, such as acrylonitrile and methacrylonitrile; acrylic acid, methacrylic acid and their esters and amides, such as methyl, ethyl, n-butyl and 2-ethylhexyl acrylates and methacrylates, and acrylamide and methacrylamide; maleic anhydride; maleic and fumaric acids and their esters; vinyl halo and vinylidene halo compounds, such as, vinyl chloride, vinyl bromide, vinyl fluoride, vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl adipate, allyl benzoate, diallyl phthalate, allyl ethyl carbonate, triallyl phosphate, diallyl fumarate and diallyl carbonate; acrolein; methyl vinyl ketone; vinylcarbazole, vinylpyrrolidone; vinylpiperidone; and mixtures thereof.

In preparing azo-copolymers, it is essential that the initial copolymerization be carried out at temperatures at which the structure (I) compound is stable. This can easily be accomplished by carrying out the copolymerization using a lower temperature initiator (either free radical, anionic, cationic or Ziegler type polymerization catalyst). The use of the structure (I) azo compound is of particular advantage in this application since it does not undergo induced decomposition when radicals are formed by a lower temperature initiator. Peroxides are susceptible to such attack. The resultant copolymer can now be used to initiate a subsequent polymerization upon heating or upon irradiation with ultraviolet light. The distance between (or concentration of) the azo groups along the polymer chain can be varied by varying the concentration of the structure (I) compound or the structure of the (I) compound in the copolymerization.

The percentage of the polymerizable azo in the (co)polymerization may be varied from 0.01 to 100% depending upon the concentration of azo groups along the polymer chain desired. The primary (co) polymer can then be mixed with one or more vinyl monomers such as given above and the copolymerization initiated by heating the mixture above the decomposition temperature of the azo group, i.e. 40°–140° C. depending on the structure of (I) or by irradiating the mixture with ultraviolet light. The copolymerizations may be carried out in suspension, bulk, solution or emulsion.

In using the structure (I) compound to prepare monomer-terminated copolymers, it is advantageous to pick a structure (I) compound whose vinyl double bond is less reactive than that of the vinyl monomer so that only the vinyl monomer will be polymerized and the vinyl group of the initiator will be left intact at the end of the chain for the subsequent graft copolymerization. It is also advantageous that the vinyl group of the azo initiator have a reactivity ratio similar to or larger to that of the second vinyl monomer in the subsequent graft copolymerization so that an appreciable amount of graft copolymer will form. Again the number of grafts in the copolymer may be varied by varying the structure of the vinyl group in (I) and/or the concentration of the azo containing polymer.

The initial polymerizations may be initiated by heating the (I) compound above its decomposition temperatures (40° C.–140° C. depending on the strucuture of I) or by irradiating them with ultraviolet light in the presence of one or more of the monomers listed above.

The resultant polymer containing vinyl end groups can subsequently be copolymerized with the second vinyl monomer such as listed above using free radical, cationic, anionic or Ziegler type polymerization initiators. The distance between grafts in the resultant graft copolymer can be varied by varying the concentration of the vinyl containing polymer in the copolymerization or by varying the structure of the vinyl group in the vinyl containing copolymer.

The concentration of the various monomer units in the copolymer can be altered to obtain the desired properties in the finished graft copolymer. The graft copolymers are good compatabilizing agents for mixtures of the individual homopolymers and are also useful in a variety of applications as discussed above.

In addition to their specific use of preparing block and graft copolymers, the structure (I) compound is useful as free radical generators, polymerization initiators for vinyl monomers (see Examples 2, 17, 18, 19 and 29), curing agents for polyester resins (see Examples 8, 9 and 10), initiators for free radical initiated chemical reactions, blowing agents for producing foamed polymers and plastics (see Example 26), selective oxidizing agents and generators of reactant free radicals.

The structure (I) compound evolves one mole of nitrogen gas per azo group in the compound when it decomposes. In addition, other gases are evolved from the breakdown and/or disproportionation of the radicals formed. Thus, the structure (I) compound is useful in applications where copious quantities of gases are desired such as in producing foamed polymers (see Example 26).

The azo-containing polymers prepared from the structure (I) compound (such as prepared in Examples 4, 11, 12, 13, 20, 21 and 24) are also useful as blowing agents for producing foamed polymers as illustrated by Example 25.

The structure (I) compound can be homopolymerized using a free radical initiator active below the decomposition temperature of the azo function in the structure (I) compound (see Example 14). The resultant azo-containing homopolymer is useful as a blowing agent for preparing foamed polymers or as a polymeric-azo initiator for polymerizing vinyl monomers (see Example 15).

One of the preferred uses for the structure (I) compound is where the azo function is used as an initiator, either alone or in conjunction with other initiators, for improved vinyl monomer polymerizations. Because the structure (I) compound is a monomer as well as an azo initiator, certain advantages are obtained when it is used as an initiator for vinyl monomer polymerization as compared to using conventional initiators; it allows for producing polymers of higher molecular weight and at faster rates than when using equimolar concentrations of conventional initiators of comparable activity, i.e., wherein both initiators have the same decomposition rates at the same temperatures (or the same half life temperature characteristics) (see Examples 17 and 19). This is an unusual result since in classical free radical polymerization kinetics, faster polymerization rates are always accompanied by lower polymer molecular weights.

The structure (I) compound, when used as an initiator, not only produces polymers of higher molecular weight but also with broader molecular weight distributions as illustrated in Example 18. Polymers with broader molecular weight distributions are desirable in many fabricating operations where high speed processing is essential. The broader molecular weight distribution causes the polymer to flux and flow at lower temperatures and at faster rates, thus allowing for processing at faster rates and/or at lower temperatures; consequently, lower energy requirements are needed. In the prior art, broader molecular weight distributions are generally obtained by adding additional materials such as chain transfer agents, special monomers, etc. to the polymerization system (see U.S. Pat. No. 4,029,869 wherein allyl methacrylate is added to a styrene polymerization to broaden the molecular weight distribution of polystyrene). When the structure (I) compound is used as initiator, no extra additives are necessary to obtain broader polymer molecular weight distributions. Moreover, higher molecular weights and/or faster rates are additional advantages of using the structure (I) compound.

This ability of structure (I) compound to increase rates and molecular weights simultaneously, when it is used as a vinyl monomer initiator, offers the polymer manufacturer some very significant advantages and versatility not possible with conventional initiators. For example, by proper choice of structure (I) compound, temperature, time, concentration, and co-initiator, the polymer manufacturer can obtain a polymer of the same molecular weight he is now producing but in a significantly shorter time cycle. Since polymer properties are mainly determined by their molecular weight, a manufacturer is able to produce more polymer per unit time in the same equipment he is now using without sacrificing polymer properties. The manufacturer can therefore increase his capacity without investing in more capital equipment and produce essentially the same quality polymer he has been previously producing. The ability to produce the same quality polymer is extremely important since the markets are already established. Customers' (fabricators') equipment is finely tuned to process a given polymer and any changes in polymer quality can raise havoc in the fabricators' plant. With conventional initiators, it is not possible to obtain faster rates without sacrificing polymer properties.

The structure (I) compound also offers the manufacturer the opportunity to produce high molecular weight polymers than he has been producing without sacrificing production time (capacity). Higher molecular weight polymers are very desirable in many applications since they generaly possess better physical and chemical properties even though more energy may be required to process them. With conventional initiators, higher molecular weights are obtained at a sacrifice in production (cycle) time.

The structure (I) compound can also be used as an initiator to produce cross linked polymers as illustrated in Examples 17 and 27. Thus, with proper choice of structure (I) compound, monomer, concentration, temperature, and time, a vinyl monomer can be converted in one operation to a crosslinked structure without resorting to expensive polyfunctional monomers or a subsequent expensive crosslinking operation. With conventional initiators, vinyl monomers are polymerized to thermoplastic polymers unless expensive crosslinking coagents are employed. Crosslinked or thermoset polymers have desirable properties such as high thermal stability, solvent resistance, abrasion resistance, strength, etc. and are used in a variety of applications such as ion-exchange resins, wire and cable insulation, batteries and many other molded products. The structure (I) compound thus offers the manufacturer a direct method of converting a relatively cheap vinyl monomer into a crosslinked polymer, something not possible with conventional initiators without crosslinking co-agents.

The azo-monomer of structure (I) is a significant improvement over polyfunctional monomer co-agents in its applications since the latter are limited to work with monomers wherein reactivity ratios are compatible. The azo portion of the structure (I) compound is not so limited since it breaks down to free radicals which will react with any free radical polymerizable vinyl functionality.

The following are some typical structure (I) compounds of this invention:

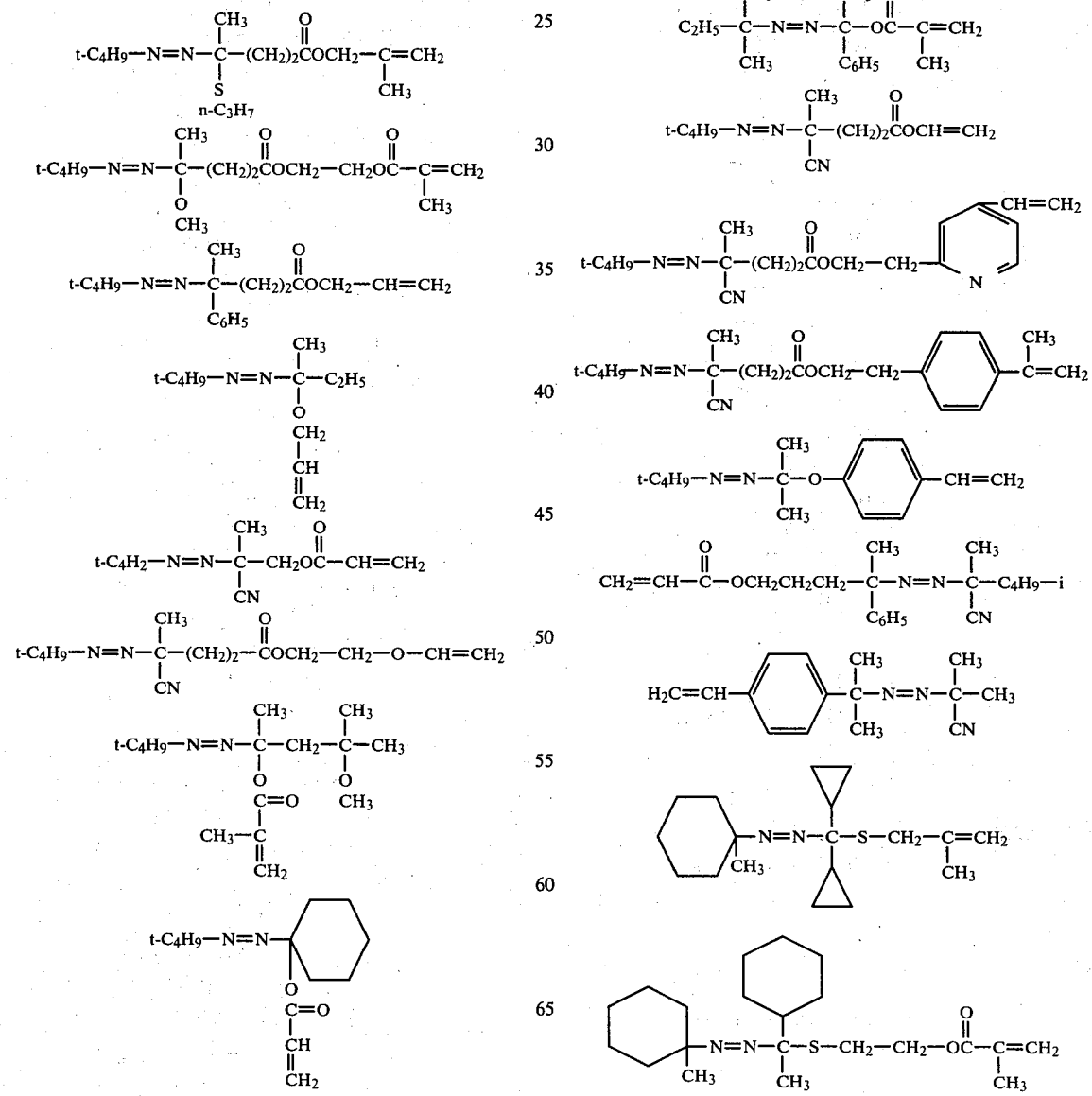

-continued
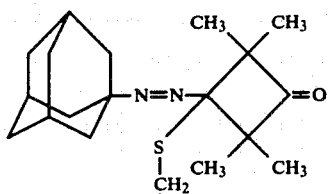
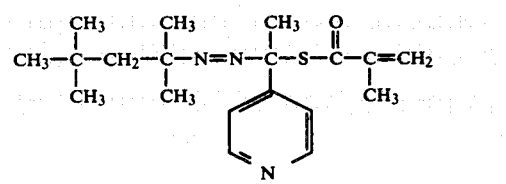
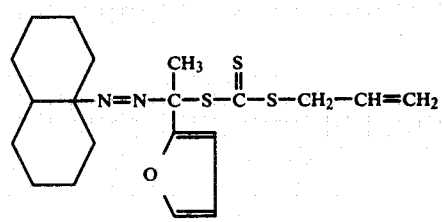
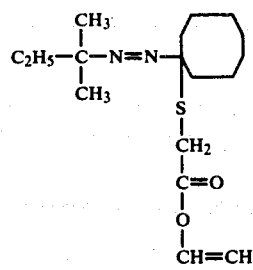
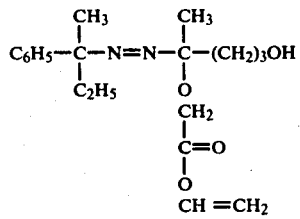
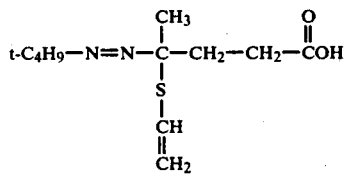
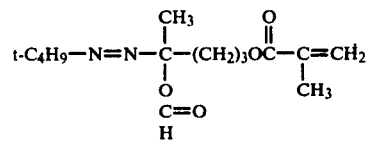
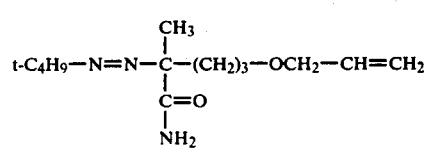
-continued
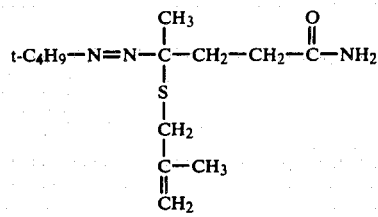
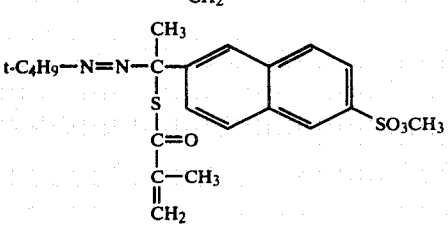
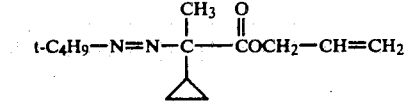
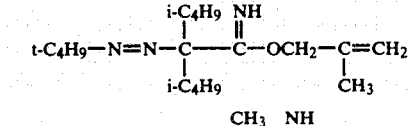
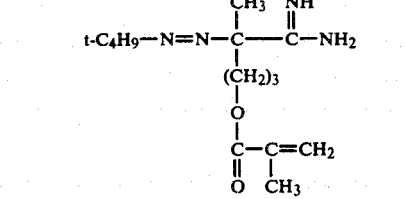
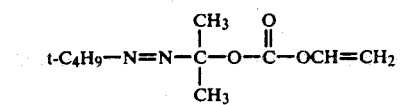
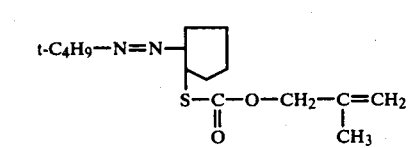
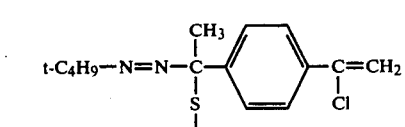
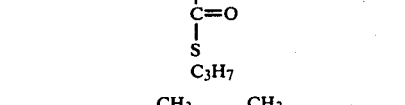
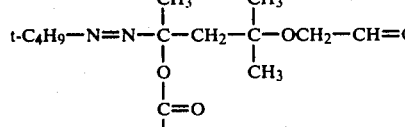
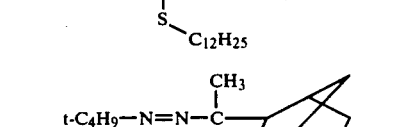
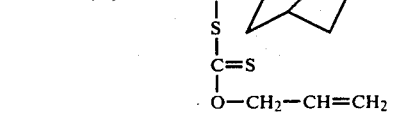

-continued

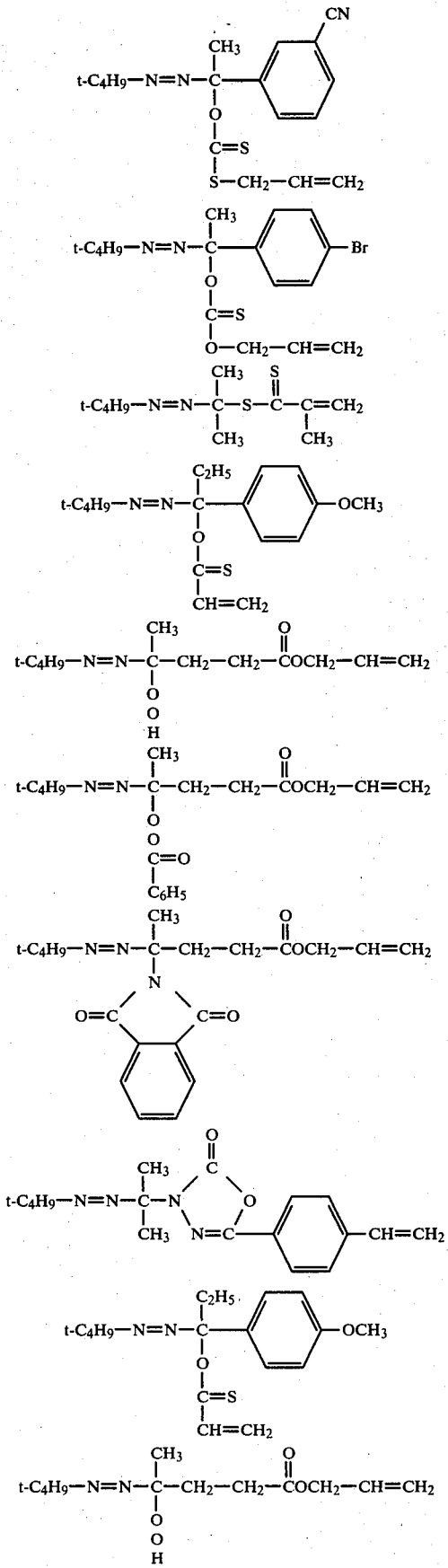

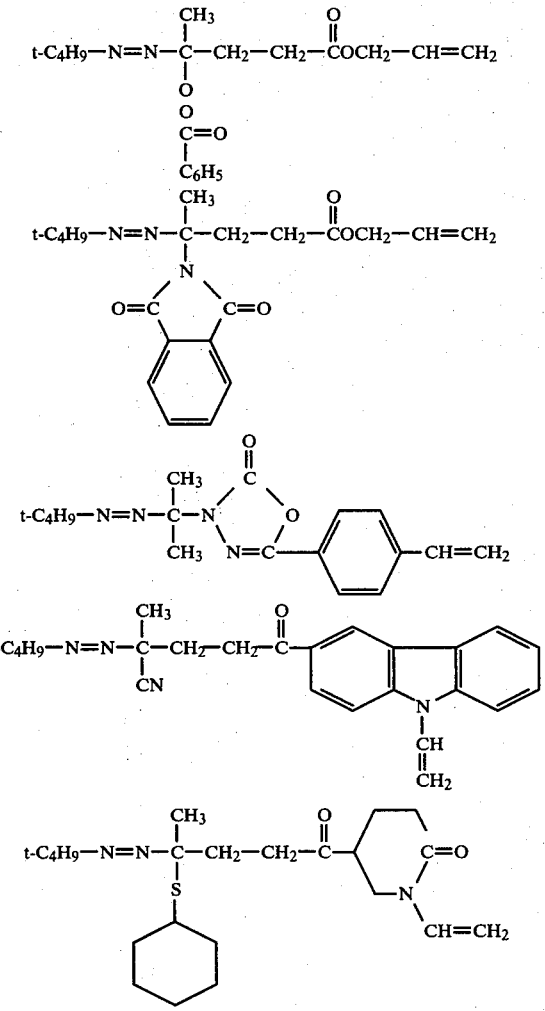

Thus having described the invention, it is further illustrated but not limited by the following working examples:

EXAMPLE 1

Preparation of Allyl 4-t-Butylazo-4-cyanovalerate

To a solution of 2.32 g (0.040 m) of allyl alcohol and 10 ml of pyridine in 50 ml of ether cooled to 10° C. in a 250 ml 4 neck round bottom flask was added a solution of 10 g (0.0435 m) of 4-t-butylazo-4-cyanovaleryl chloride* in 10 ml ether. The acid chloride solution was added dropwise holding the reaction temperature below 20° C. After the addition was complete, the reaction was stirred an additional 2 hours at room temperature and poured into 100 ml water. The ether layer was separated, washed with 20 ml portions of 10% HCl, 10%, NaHCO₃ and water. The ether solution was dried over anhydrous sodium sulfate, filtered and the ether evaporated off. The crude produce weighed 8.95 g (89%). The infrared spectra indicated there was a small amount of unreacted acid chloride present in the product. The crude product was purified by column chromatography over alumina using pentane as the eluent. The acid chloride did not come off the column. The pentane was evaporated off to leave the pure product.

*4-t-Butylazo-4-cyanovaleryl chloride was prepared from 4-t-butyl-azo-4-cyanovaleric acid and thionyl chloride or phosphorous pentachloride (see U.S. Pat. No. 3,752,802).

EXAMPLE 2

Preparation of a Styrene-Vinyl Acetate Copolymer using Allyl 4-t-Butylazo-4-cyanovalerate Five drawn test tubes were each filled with 5 grams of styrene and 1 gram of allyl 4-t-butylazo-4-cyanovalerate (from Example 1) and sealed under nitrogen. They were placed in a 70° C. bath until the viscosity was noted as being almost nonflowable. This occurred after 4 hours at 70° C. The tubes were removed from the bath, cooled to room temperature, cracked open and the gummy masses allowed to dissolve in 5 separate breakers containing about 75 ml benzene each. The benzene solutions containing the dissolved polystyrene were each poured into a liter of odorless mineral spirits (OMS). The combined precipitates were reprecipitated from benzene-OMS two more times, filtered and dried. The compound contained approximately 0.05 moles of ester group (from initiator) per gram of sample.

Into a 100 ml 4 neck flask was weighed 10 g of vinyl acetate and 5 g of the above polystyrene and 1.2 g 49% diisobutyryl peroxide. The reaction was stirred magnetically at 30° C. for 1½ hours. The mass became quite viscous during this period. Hydroquinone and chloroform were added to the flask and stirring continued over the weekend. The polymer which had dissolved in the chloroform over the weekend was precipitated in OMS forming a gummy mass. The product was then reprecipitated from benzene into OMS three times, filtered and dried. The product weighed 9.7 g.

The presence of a graft styrene-vinyl acetate copolymer was demonstrated by running compatability tests of the homopolymers in benzene, both with and without the graft copolymer. A 1 to 1 mixture of 6% polystyrene in benzene and 6% polyvinyl acetate in benzene was prepared in a capped vial and shaken for 10 minutes and then allowed to stand untouched. Phase separation was observed after 1 hour. On the other hand, a 1 to 1 mixture of 6% solutions of polystyrene in benzene, polyvinyl acetate in benzene and of the styrenepolyvinyl acetate graft copolymer was prepared in a capped vial and shaken for 10 minutes and then allowed to stand untouched. Phase separation had not begun after 10 days at which time the test was terminated. It was concluded that the graft copolymer was formed and that it also was a good compatabilizing agent for polystyrene and polyvinyl acetate.

EXAMPLE 3

Preparation of 2-(Methacryloxy)ethyl 4-t-Butylazo-4-cyano-valerate(MEBC)

To a solution of 6.5 g (0.05 m) of 2-hydroxyethyl methacrylate and 5 ml of pyridine in 50 ml methylene chloride in a 100 ml 4 neck round bottom flask was added dropwise 11.4 g (0.05 m) of 4-t-butylazo-4-cyanovaleryl chloride over 15 minutes at 25° C. The reaction was then allowed to stir overnight. The next morning the reaction mixture was poured into water and the methylene chloride layer separated, washed with 10% HCl, water, 10% NaHCO$_3$ and water. The methylene chloride layer was dried over anhydrous sodium sulfate, filtered and the methylene chloride stripped off leaving 14.6 g (91%) of a clear brown liquid. The product was stored in the refrigerator.

EXAMPLE 4

Copolymerization of Methyl Methacrylate and 2-(Methacryloxy)-ethyl 4-t-Butylazo-4-cyanovalerate (MEBC)

To a solution of 20 g of methyl methacrylate and 0.4 g of 2-(methacryloxy)ethyl 4-t-butylazo-4-cyanovalerate (from Example 3) in 20 g of benzene under a nitrogen atmosphere was added 0.5 g of acetyl cyclohexylsulfonyl peroxide and the reaction mixture stirred for 6 hours at 40° C. During the first five hours of the reaction a solution of 1.6 g of 2-(methacryloxy)ethyl 4-t-butylazo-4-cyanovalerate (MEBC) in 10 ml of benzene was added dropwise. A viscous solution resulted at the end of the reaction period. The copolymer was precipitated from methanol and dried to give a 67% yield. The copolymer was then purified by reprecipitating it 3 times. The resultant copolymer was then used for initiating styrene polymerization (Example 5).

EXAMPLE 5

Bulk Copolymerization of Styrene and the Azo-Containing Polymethyl methacrylate of Example 4

Into a drawn test tube was placed 0.5 g of the azo-containing polymethyl methacrylate of Example 4 and 1 g of styrene monomer. The tube was sealed under an atmosphere of nitrogen and immersed in an 80° C. oil bath for 2.5 hours and then allowed to cool slowly. After cooling to room temperature, the test tube was cracked open and the copolymer precipitated from methanol and dried. A conversion of 47% was obtained. Styrene under similar conditions without the azo-containing copolymer gives only 1.5% conversion.

A 0.39 g sample of the graft copolymer stabilized a mixture of two 3 g 13% solutions of the homopolymers in chloroform demonstrating that a graft copolymer was formed.

EXAMPLE 6

Preparation of Allyl 4-t-Butylazo-4-chlorovalerate

The t-butylhydrazone of allyl levulinate was prepared by refluxing an aqueous solution of t-butylhydrazine and an equivalent amount of allyl levulinate, cooling the mixture and separating the organic layer.

Into a −25° C. solution of 8.7 grams (0.0385 moles) of the t-butylhydrazone of allyl levulinate and 3.92 grams (0.0385 moles) of triethylamine in 100 ml of pentane was passed 2.73 grams (0.0385 moles) of chlorine. After the addition was complete, the reaction was stirred for 15 minutes and slowly warmed to −5° C. and filtered. The triethylamine hydrochloride filter cake was washed with pentane and the filtrates combined and the pentane evaporated on a rotating evaporator leaving 8.7 grams (87% yield) of a light yellow liquid. The infrared (IR) spectrum of the product was in agreement with the structure of allyl 4-t-butylazo-4-chlorovalerate.

EXAMPLE 7

Preparation of Allyl 4-(t-Butylazo)-4-(t-butylperoxy)valerate

Allyl 4-t-butylazo-4-chlorovalerate was prepared by chlorinating the t-butylhydrazone of allyl levulinate in pentane (see Example 6).

To a solution of 2.32 grams (0.0352 moles) of 85% potassium hydroxide in 10 ml of water, cooled to 15° C. in a 50 ml erlenmeyer flask was added 4.5 grams (0.045 moles) of 90% t-butyl hydroperoxide slowly and with rapid stirring. After the addition was complete, the reaction was stirred for 15 minutes at 15° C. and then 8.32 grams (0.032 moles) of allyl 4-t-butylazo-4-chlorovalerate was added dropwise over a 15 minute period holding the temperature at 15°-20° C. After the was complete the reaction was stirred for 90 minutes at 0°-5° C. A one gram portion of 50% NaOH was then added and the reaction stirred for 15 minutes to remove the excess t-butyl hydroperoxide. Ice water was then added until the potassium chloride dissolved. The mixture was extracted with 25 ml cold pentane, the pentane extract washed with ice cold water, saturated NaHCO$_3$ solution, dried over anhydrous sodium sulfate, filtered and the pentane evaporated under reduced pressure at 10° C. to leave 6.6 grams (66% yield) of crude allyl 4-(t-butylazo)-4-(t-butylperoxy)valerate. The product was stored in a dry ice chest.

EXAMPLE 8

Curing an Unsaturated Polyester-Styrene Resin with Allyl 4-(t-Butylazo)-4-(t-butylperoxy)valerate An unsaturated polyester resin was made by reacting maleic anhydride (1.0 mole), phthalic anhydride (1.0 mole), and propylene glycol (2.2 moles) until an acid number of 45-50 was obtained. To this was added hydroquinone at a 0.013% concentration. Seven parts of this unsaturated polyester were diluted with 3 parts of monomeric styrene to obtain a homogeneous blend having a viscosity of 13.08 poise and a specific gravity of 1.14.

To 20 grams of this blend was added 0.2 grams of crude allyl 4-(t-butylazo)-4-(t-butylperoxy)valerate (from Example 7) and the mixture stirred up well with a wooden spatula. The internal temperature was recorded as a function of time and a peak exotherm of 318° F. (158° C.) was reached in 2.9 minutes indicating an excellent cure of the unsaturated polyesterstyrene resin blend had occurred. The resultant cured material was very hard and was water white in color.

Without an initiator, no cure of this resin blend occurred even after more than 30 minutes at 212° F. (100° C.).

EXAMPLE 9

Preparation of Allyl 4-t-Butylazo-4-azidovalerate

To a cold solution of 2.6 grams (0.04 moles) of sodium azide in 50 ml of 70% aqueous methanol in a 200 ml beaker was added 9.75 grams (0.0375 moles) of allyl 4-t-butylazo-4-chlorovalerate dropwise, controlling the temperature at 5°-10° C. with an ice bath. After the addition was complete, the reaction was stirred for 45 minutes at room temperature, poured into 150 ml of water and the product extracted with pentane. The pentane solution was separated, washed with water, saturated NaHCO$_3$, water, dried over anhydrous sodium sulfate, filtered and the pentane evaporated to leave 5.8 grams (58% yield) of a light yellow liquid. The infrared specturm of the product was in agreement with the structure of allyl 4-t-butylazo-4-azidovalerate.

At a 1.0 weight percent loading the allyl 4-t-butylazo-4-azidovalerate cured the unsaturated polyester-styrene resin of Example 8 at 115° C. giving a peak exotherm of 406° F. (208° C.) in 3.4 minutes and a very hard cured resin.

EXAMPLE 10

Preparation of Allyl 4-t-Butylazo-4-thiophenoxyvalerate

To a cold solution of 2.04 grams (0.031 moles) of 85% potassium hydroxide and 3.59 grams (0.032 moles) of thiophenol in 50 ml of methanol was added 7.8 grams (0.03 moles) of allyl 4-t-butylazo-4-chlorovalerate dropwise, controlling the temperature at 10° C.±2° C. with an ice bath. After the addition was complete, the reaction was stirred for 40 minutes at room temperature, and the reaction mixture poured into 150 ml of water. The product was extracted with pentane, the pentane solution separated, washed with water, saturated NaHCO$_3$, water, dried over anhydrous sodium sulfate, filtered and the pentane evaporated under reduced pressure to leave 8.8 grams (88% yield) of a light yellow liquid. The infrared specturm of the product was in agreement with the structure of allyl 4-t-butylazo-4-thiophenoxyvalerate.

At a 1.0 weight percent loading the allyl 4-t-butylazo-4-thiophenoxyvalerate cured the unsaturated polyester-styrene resin of Example 8 at 130° C. giving a peak exotherm of 396° F. (202° C.) in 7.8 minutes and a very hard cured resin.

EXAMPLE 11

Copolymerization of MEBC with Methyl Methacrylate (MMA)

Solution polymerizations in toluene at 45° C. were carried out in sealed tubes under nitrogen using di(sec-butyl) peroxydicarbonate as initiator. Conversions were restricted to >10%. The polymers were precipitated from cooled heptane and purified by one reprecipitation from toluene into cooled heptane before vacuum drying. Copolymer compositions were calculated from elemental analyses for nitrogen, based on a nitrogen content of 12.3 wt.% found for the homopolymer of MEBC (theoretical 12.99%). Actual amounts of reactants are detailed below: in addition to the listed materials each tube contained toluene (16 ml) and di(sec.-butyl) peroxydicarbonate (0.020 g). Feed and copolymer compositions are shown.

| Sample | MMA(g) | MEBC(g) | Wt. % N in Polymer | Mole % MEBC in Feed | Mole % MEBC in Copolymer |
|---|---|---|---|---|---|
| 1 | 0.1427 | 3.8564 | 11.4 | 89.3 | 79.7 |
| 2 | 0.3081 | 3.6286 | 11.0 | 78.5 | 72.3 |
| 3 | 0.3999 | 3.6003 | 10.8 | 73.6 | 69.0 |
| 4 | 1.0000 | 3.0000 | 8.6 | 48.2 | 41.8 |
| 5 | 2.0000 | 1.9994 | 6.63 | 23.6 | 26.6 |
| 6 | 2.2857 | 1.7144 | 5.32 | 18.8 | 19.0 |
| 7 | 3.0002 | 1.1002 | 3.41 | 10.2 | 10.6 |
| 8 | — | 4.0000 | 12.3 | 100 | 100 |

Reactivity ratios were calculated from the copolymer compositions by the method of Yezrielev, Brokhina and Roskin (Polymer Science USSR 11 1894 (1969)). Where MEBC is $M_1$ and the reactivity ratios are:

$r_1 = 0.4722$ s.d. 0.0617

$r_2 = 0.8262$ s.d. 0.0756

These data illustrate that random copolymers can easily be prepared from MEBC and MMA.

EXAMPLE 12

Copolymerization of MEBC with Styrene

A similar series of solution copolymerizations were carried out using styrene as the comonomer. The only essential difference being that methanol was used as the precipitant rather than heptane. Monomer feeds and corresponding copolymer compositions are detailed below.

| Sample | Mole % MEBC in Feed | Mole % MEBC in Copolymer |
|---|---|---|
| 1 | 78.57 | 63.80 |
| 2 | 61.69 | 54.11 |
| 3 | 55.04 | 49.30 |
| 4 | 28.86 | 33.48 |
| 5 | 11.40 | 17.87 |
| 6 | 9.14 | 15.39 |
| 7 | 4.44 | 8.23 |

Reactivity ratios were calculated by the method of Example 1, where MEBC is $M_1$, $r_1 = 0.2826$ s.d. 0.0124

$r_2 = 0.4771$ s.d. 0.0049

EXAMPLE 13

Copolymerization of MEBC with Ethyl Acrylate

Solution polymerizations were carried out by the method of Example 12. Monomer feeds and corresponding copolymer compositions are detailed below.

| Sample | Mole % MEBC in Feed | Mole % MEBC in Copolymer |
|---|---|---|
| 1 | 89.3 | 81.6 |
| 2 | 85.5 | 81.1 |
| 3 | 83.3 | 74.0 |
| 4 | 48.1 | 67.4 |
| 5 | 23.6 | 55.1 |
| 6 | 18.9 | 53.9 |
| 7 | 9.34 | 23.3 |

Reactivity ratios were calculated by the method of Example 1. Where $M_1$ is MEBC $r_1 = 0.4587$ s.d. 0.1013

$r_2 = 0.0915$ s.d. 0.0719

EXAMPLE 14

Homopolymerization of MEBC

The polymerization was carried out in a sealed tube under nitrogen at 45° C.

Reactants:

| MEBC | 2.0 g |
|---|---|
| Toluene | 8.0 ml |
| di(sec.-butyl)peroxydicarbonate | 0.02 g |

The polymerization was allowed to continue for five hours at which point the solution was cooled and the polymer was precipitated from cooled heptane. Some material may have been lost in the process, as the material precipitated as a gum. After vacuum drying the polymer yield was 1.32 g.

EXAMPLE 15

Use of the Homopolymer from Example 4 to Polymerize MMA

The polymerization was carried out in a sealed tube under nitrogen at 100° C.

Reactants:

| Polymer from Example 14 | 0.030 g |
|---|---|
| MMA | 3.0 ml |
| Toluene | 27.0 ml |

The polymerization was allowed to continue overnight. On removal from the heating bath, the tube contained a highly swollen gel.

EXAMPLE 16

Use of Copolymer #7 from Example 11 to Polymerize MMA

Reactants:

| Copolymer #7 | 0.1135 g |
|---|---|
| MMA | 1.157 g |
| Toluene | 2.516 g |

The polymerization was carried out in a sealed tube under nitrogen at 100° C., and was allowed to continue for 8 hours. When the tube was removed from the bath, it contained a swollen gel.

EXAMPLE 17

Use of MEBC to Polymerize Styrene

Bulk polymerizations of styrene were carried out in sealed tubes under nitrogen at 100° C. It was found that if MEBC was employed as the sole initiator a gel resulted, but the use of combinations of MEBC with a conventional azo initiator of similar reactivity (2-t-butylazo-2-cyanopropane) gave soluble polymers. The total initiator concentration was kept constant at $1.3 \times 10^{-2}$ mol $1^{-1}$ and relative amounts of MEBC and 2-t-butylazo-2-cyanopropane (TBCP) varied. All polymerizations were allowed to continue for 15 ½ hours at which point the tubes were opened and the polymer dissolved in toluene. The polymer was recovered by precipitation from methanol and dried under vacuum. Molecular weights were measured by membrane osmometry in toluene at 40° C.

| Sample | Mole % MEBC in Total Initiator | $\overline{M}_n$ |
|---|---|---|
| 1 | 0 | 134,801 |
| 2 | 20 | 151,485 |
| 3 | 30 | 190,773 |
| 4 | 40 | 243,630 |
| 5 | 50 | 235,384 |
| 6 | 60 | 273,214* |
| 7 | 100 | crosslinked gel |

| | Conversion % | |
|---|---|---|
| Time Hours | TBCP | 70:30, TBCP:MEBC |
| 1.13 | 34.5 | 41.5 |
| 2.17 | 49.6 | 52.5 |
| 3.93 | 67.2 | 71.4 |

-continued

| 6.13 | 91.0 | 94.7 |

*This sample contained a very small gel fraction. The rate of polymerization due to TBCP at $1.32 \times 10^{-2}$ mol $1^{-1}$ was compared to that due to a 70:30 mol % combination of TBCP and MEBC having a total concentration of $1.32 \times 10^{-2}$ mol $1^{-1}$. Four tubes with a known amount of styrene, for each initiator system, were sealed under nitrogen and polymerized at 100° C. The tubes were removed from the heating bath at intervals, the polymer dissolved in toluene and precipitated from methanol. The dried polymers were used to calculate % conversions.

Thus the substitution of 30% of the TBCP by an equimolar amount of MEBC causes both the rate and the molecular weight to increase. Using conventional free radical initiators the molecular weight of the resultant polymer decreases as polymerization rate increases. The tendency of MEBC to cause crosslinking could find use in the preparation of polymers for use in ion exchange resins.

EXAMPLE 18

U.S. Pat. No. 4,029,869 describes the use of allyl methacrylate to broaden the molecular weight distribution of polystyrene. The present example shows that MEBC can also be used to broaden molecular weight distributions, but also has the additional advantages of acting as an initiator at the same time, and of increasing the molecular weight of the polystyrene thus giving a potential for reducing cycle time.

Bulk styrene polymerizations were carried out under nitrogen in selected tubes. The tubes were heated to 125° C. over 2 hours then held at that temperature for a further 4 hours. t-Butyl perbenzoate was used as the initiator. At the end of the polymerization, the polymers were dissolved in toluene and precipitated from methanol. The isolated polymers were filtered off and dried under vacuum. Molecular weights were measured by gel permeation chromatography. The following table compares the effects of MEBC and allyl methacrylate on the molecular weight distribution.

| | Concentration phm. | | | | | | |
|---|---|---|---|---|---|---|---|
| t-butyl-perbenzoate | 0.15 | 0.15 | 0.15 | 0.15 | 0.15 | 0.105 | 0.075 |
| allyl methacrylate | — | 0.10 | 0.20 | 0.30 | — | — | — |
| MEBC | — | — | — | — | 0.05 | 0.075 | 0.188 |
| $\overline{M}_w \times 10^{-5}$ | 2.53 | 3.14 | 3.81 | 4.64 | 3.24 | 3.93 | 5.54 |
| $\overline{M}_n \times 10^{-5}$ | 1.03 | 1.13 | 1.16 | 1.27 | 1.22 | 1.34 | 1.44 |
| $\overline{M}_w/\overline{M}_n$ | 2.46 | 2.78 | 3.28 | 3.65 | 2.66 | 2.93 | 3.85 |

EXAMPLE 19

Use of MEBC to Polymerize Methyl Methacrylate

Two solutions were prepared.

| | 1 | 2 |
|---|---|---|
| Toluene | 60 ml | 60 ml |
| MMA | 15 ml | 15 ml |
| MEBC | 0.1817 g | — |
| TBCP | — | 0.0859 g |

The solutions were divided in known amounts into tubes (3 tubes for each solution), flushed with nitrogen and sealed. The polymerization was performed at 90° C. and tubes were removed at intervals. The polymers were recovered by precipitation from methanol and dried under vacuum.

| | Conversion % | |
|---|---|---|
| Time hours | 1 | 2 |
| 1 | 33.4 | 25.2 |
| 2 | 58.4 | 42.9 |
| 3 | 65.4* | 55.8* |

*The molecular weights of these polymers were determined from osmotic pressure measurements in toluene at 40° C.
1 $\overline{M}_n = 64{,}700$
2 $\overline{M}_n = 52{,}600$
Thus the replacement of TBCP by MEBC results in a simultaneous increase in rate of polymerization and molecular weight.

EXAMPLE 20

Preparation of a Stearyl-methacrylate (SMA) MEBC Copolymer

The copolymerization was carried out in a two neck round bottom flask equipped with nitrogen inlet and reflux condenser. The continuous passage of nitrogen was used to agitate the solution.

The following reactants were charged to the flask.

| SMA | 250 g |
| MEBC | 6.25 g |
| di(sec.-butyl)peroxydicarbonate | 10 g |
| Toluene | 1250 ml |

The polymerization was allowed to continue for 16 hours at 45° C. before cooling the solution and isolating the polymer by precipitation from methanol. The precipitated polymer was filtered off and dried under vacuum. Yield 195.7 g.

EXAMPLE 21

Preparation of an Ethyl Acrylate (EA)-MEBC Copolymer

The copolymerization was carried out in a round bottom flask similar to that described in Example 20. Reactants:

| EA | 92.6 g |
| MEBC | 7.5 g |
| di(sec.-butyl)peroxydicarbonate | 0.5 g |
| Toluene | 400 ml |

The polymerization was continued for 1 hour at 45° C. before precipitating the polymer from cooled heptane. The precipitated polymer was filtered off and vacuum dried. Yield 40.0 g.

EXAMPLE 22

Use of Polymer from Example 20 to Polymerize Styrene

The polymer from Example 10 was used to polymerize styrene, thus preparing a stearyl methacrylate/styrene graft copolymer.

The following reactants were sealed in a test tube under nitrogen.

| Styrene | 20 g |
| Polymer from Example 20 | 2.0 g |
| Dicumyl peroxide | 0.05 g |

The polymerization was continued for 2 hours at 100° C. plus 16 hours at 120° C. The polymer casting was translucent with an opalescent blue tint, rather like high impact polystyrene with a low rubber content.

EXAMPLE 23

Use of the Polymer from Example 21 to Polymerize MMA

A solution of the polymer from Example 21 (2.0 g) in MMA (20 ml) was prepared. Trial castings were polymerized in ⅛" I.D. glass tubes which were flushed with nitrogen before sealing. Polymerization temperatures between 55° C. and 100° C. were all successful in producing clear castings, though those produced at higher temperatures contained some voids due to the higher exotherms produced. The castings are completely transparent, and due to their rubber content, would be expected to have higher impact-strengths than poly MMA.

EXAMPLE 24

Preparation of a Copolymer of MEBC with MMA

The polymerization was conducted in a sealed tube under nitrogen.

Reactants:

| MMA | 0.143 g |
|---|---|
| MEBC | 3.856 g |
| di(sec.-butyl)peroxydicarbonate | 0.021 g |
| Toluene | 16 ml |

The polymerization was continued for 2.33 hours at 45° C., before precipitating the polymer from methanol. The precipitated polymer was filtered off and dried under vacuum. Yield 1.212 g.

EXAMPLE 25

Use of the Copolymer from Example 24 to Foam a Polyester Resin

Formulation:

| Laminac 4123* | 10 ml |
|---|---|
| Polymer from Example 24 | 0.6 g |
| Dow 193 Surfactant** | 0.1 ml |
| di(sec.-butyl)peroxydicarbonate | 0.1 ml |

*A general orthophthalic resin manufactured by American Cyanamid Company.
**Manufactured by Dow Corning Company, a low molecular weight silicone glycol copolymer.

The above formulation was successfully foamed in an open test tube immersed in an oil bath at 110° C. The density of the foam was approximately 0.48 g ml$^{-1}$.

EXAMPLE 26

Use of MEBC to Foam a Polyester Resin

Formulation:

| Laminac 4123* | 100 ml |
|---|---|
| MEBC | 5 ml |
| Dow 193 Surfactant* | 1 ml |
| di(sec.-butyl)peroxydicarbonate | 2 ml |

See Example 25.

The above formulation was successfully foamed in a metal mold in a press at 225° F. The foam block had an overall density of 0.56 g ml$^{-1}$.

EXAMPLE 27

Use of MEBC to Prepare Cross-linked Polystyrene Beads

The beads were prepared by suspension polymerization in a sealed reactor which was immersed in an oil bath.

Aqueous phase:

| Triple distilled water | 447.5 ml |
|---|---|
| 1% solution of poly(vinyl alcohol) (Dupont Elvanol 50-42) | 50 ml |
| 0.1% solution of surfactant (GAF Emulphogene BC-840) | 2.5 ml |

The aqueous phase was charged to the reactor which was then heated to 90° C.

| Monomer phase: | |
|---|---|
| Styrene | 250 g |
| MEBC | 0.5 g |
| Dicumyl peroxide | 0.126 g |

The monomer/initiators were added to the reactor with stirring, the air space was flushed with nitrogen and the reactor sealed. The polymerization was continued for 2 hours at 90° C., 2 hours at 125° C. and 2 hours at 145° C. At the end of the polymerization, the beads were filtered off and dried under vacuum. A sample of the beads (2.013 g) was allowed to stand in toluene (150 ml) for two days. After this time the liquid was filtered off, the weight of the swollen gel was 46.084 g. The soluble portion of the polymer was precipitated by pouring the filtrate into a large excess of methanol. The precipitated polymer was filtered off and dried under vacuum. The dry weight was 1.055 g.

Hence, of the polystyrene in the beads, 52.41% is soluble. The degree of crosslinking of the insoluble portion was estimated from $$\frac{\text{weight of insoluble portion swollen in toluene}}{\text{dry weight of insoluble portion}} = 48.104$$

The experiment was repeated with the amount of MEBC increased to 2.502 g i.e. an increase from 0.2 to 1.0 phm. An analysis of the beads showed that 9.16% of the polymer was soluble in toluene and the swelling ratio of the insoluble portion was 17.75.

Hence, an increase in the concentration of the azo compound has brought about an increase in the degree of crosslinking. In contrast to conventional initiators, where an increase in concentration causes a reduction in the molecular weight of the resultant polymer.

EXAMPLES 28-33

Preparation of Allyl 4-Substituted-4-(t-amylazo)valerates

A. Preparation of Allyl Levulinate t-Amylhydrazone

To a 1 liter round bottom flask equipped with a magnetic stirrer and water-cooled condenser was added 760 grams (0.5 mole) of a 9.1% aqueous solution of t-amylhydrazine hydrochloride, 78 grams (0.5 mole) of allyl levulinate and 40 grams (0.5 mole) of 50% sodium hydroxide. The flask was placed in an oil bath on a magnetic stirrer and the contents stirred and heated to reflux. The reaction was refluxed gently for 3 hours and allowed to cool to room temperature. The organic layer was separated, dried over anhydrous sodium sulfate and the drying agent removed by filtration. The yellow liquid product weighed 116 grams (96.5% crude yield). The infrared spectrum of the product contained a strong band at 1718 cm$^{-1}$ (carbonyl) and a weak band at 1620 cm$^{-1}$ (C=N) indicating that the hydrazone band had formed and the ester group was still intact.

B. Preparation of Allyl 4-t-Amylazo-4-chlorovalerate

To a 1 liter 3-neck round bottom flask, equipped with a mechanical stirrer, thermometer, chlorine inlet tube and condenser was added 96.0 grams (0.4 mole) of allyl levulinate t-amylhydrazone, 400 mls of pentane and 41.5 grams of triethylamine. The resulting solution was cooled to 5° C. and and with stirring 28.4 grams (0.4 mole) of chlorine was slowly added over 30 minutes, holding the temperature at 5° to 15° C. After the addition was complete the mixture was stirred for 10 minutes at 10° C. before adding 164 grams of 10% NaOH to neutralize the triethylamine hydrochloride that had formed. The mixture was stirred until the hydrochloride dissolved and then the aqueous layer was separated. The pentane layer was washed with saturated sodium bicarbonate solution, dried over anhydrous sodium sulfate, filtered and the pentane and triethylamine stripped off on a rotary evaporator under reduced pressure. The residue was a yellow liquid weighing 109 grams (99% crude yield). The product was used as an intermediate in preparing the following azo compounds.

C. General Procedure for the Preparation of Allyl 4-Substituted-4-(t-amylazo)valerates To a solution of 0.05–0.08 moles of the desired salt in the appropriate solvent in a 100 ml 3-neck round bottom flask, equipped with a thermometer, a condenser and magnetic stirrer, was added 0.05 moles of allyl 4-t-amylazo-4-chlorovalerate while holding the reaction temperature in the proper range with a water bath. After the addition was complete, the reaction mixture was stirred 1–1½ hours, poured into water and the organic layer taken up in 100 mls of pentane. The pentane layer was washed with water, dilute HCl, water, saturated sodium bicarbonate, dried over anhydrous sodium sulfate, filtered and the pentane stripped off on a rotating evaporator under reduced pressure. The yellow residue was weighed and the crude percent yield calculated. An infrared spectrum of the product was run and the identifying bands noted.

The experimental details are found in the following table.

Preparation of Allyl 4-Substituted-4-(t-amylazo)valerates $$C_2H_5-\underset{\underset{CH_3}{|}}{\overset{\overset{CH_3}{|}}{C}}-N=N-\underset{\underset{X}{|}}{\overset{\overset{CH_3}{|}}{C}}-CH_2-CH_2-\overset{\overset{O}{\|}}{C}OCH_2-CH=CH_2$$

| Example # | Subst. X | Moles α-chloro-azo | Salt MX | Moles MX | Solvent | mls Solvent | Reaction Temp °C. | Reaction Time (Mins) | Crude % Yield |
|---|---|---|---|---|---|---|---|---|---|
| 28 | —CN | .05 | NaCN | .07 | 75% Aq. CH$_3$OH | 60 | 15–20 | 90 | 52 |
| 29 | CH$_3$CO— (O=) | .05 | NaOAc | .07 | Acetic acid | 60 | 25 | 60 | 77 |
| 30 | CH$_3$O— | .05 | NaOCH$_3$ | .08 | CH$_3$OH | 65 | 15–20 | 60 | 45 |
| 31 | C$_6$H$_5$O— | .05 | NaOC$_6$H$_5$ | .07 | CH$_3$OH | 60 | 15–20 | 60 | 60 |
| 32 | phthalimido | .05 | Sodium phthalimide | .06 | Dimethylformamide | 50 | 35–40 | 90 | 52 |
| 33 | CH$_3$C(=O)—S— | .05 | NaSCCH$_3$ (O=) | .05 | CH$_3$OH | 50 | 15–25 | 60 | 65 |

| | Identifying IR Bands | | |
|---|---|---|---|
| Example # | Strength | Wavelength | Functional Group |
| 28 | Weak | 2200 cm$^{-1}$ | Cyano |
| | Strong | 1720 cm$^{-1}$ | Ester carbonyl |
| | Strong | 1160 cm$^{-1}$ | Carbon-oxygen |
| 29 | Strong | 1720 cm$^{-1}$ | Allyl ester carbonyl |
| | Strong | 1725 cm$^{-1}$ | Acetyl carbonyl |
| 30 | Strong | 1720 cm$^{-1}$ | Ester carbonyl |
| | Strong | 1160 cm$^{-1}$ | Ester carbon-oxygen |
| | Strong | 1280 cm$^{-1}$ | Ether carbon-oxygen |
| 31 | Strong | 1720 cm$^{-1}$ | Ester carbonyl |
| | Strong | 1160 cm$^{-1}$ | Ester carbon-oxygen |
| | Strong | 1180–1220 cm$^{-1}$ | Phenyl ether carbon-oxygen |
| 32 | Strong | 1720 cm$^{-1}$ | Ester carbonyl |
| | Strong | 1160 cm$^{-1}$ | Ester carbon-oxygen |
| | Strong | 1730–1780 cm$^{-1}$ | phthallmido carbonyls |
| 33 | Strong | 1720 cm$^{-1}$ | Ester carbonyl |
| | Strong | 1160 cm$^{-1}$ | Ester carbon-oxygen |
| | Strong | 1730 cm$^{-1}$ | Thio Acetyl Carbonyl |

EXAMPLE 34

Preparation of Allyl 4-t-Cumylazo-4-cyanovalerate (A) Preparation of t-Cumylhydrazine Hydrochloride Solution A slurry of 57.4 grams (0.3 mole) of t-cumylurea in 525 ml of 45° C. water was prepared in a 1 liter 3-neck round bottom flask which was equipped with a mechanical stirrer, thermometer, chlorine inlet tube and a condenser. With good agitation, 21.3 grams (0.3 mole) of chlorine was added over 35 minutes while holding the temperature at 40° to 45° C. After the addition was complete, the slurry was cooled to 10° C. and 54.0 grams (0.27 mole) of 20% sodium hydroxide was added while holding the temperature below 15° C. The pH was then adjusted to 7 by adding small amounts of saturated sodium bicarbonate. To the neutral slurry was added 150 ml of chloroform and the mixture stirred until the N-chloro-N'-t-cumylurea had dissolved. The chloroform layer was separated and with rapid stirring was added to a solution of 89.1 grams (1.35 mole) of 85% potassium hydroxide in 544 mls of water. The addition was made over 30 minutes while holding the temperature at 20°-25° C. The mixture was stirred an additional 15 minutes and then cooled to 10° C. and the mixture acidified to pH 2 by the addition of concentrated hydrochloric acid. The stirring was stopped and the chloroform layer was separated and discarded. The aqueous solution of t-cumylhydrazine hydrochloride was used in the next step.

(B) Preparation of Ally Levulinate t-Cumylhydrazone

The aqueous solution of t-cumylhydrazine hydrochloride from above was added to a 1 liter 3-neck round bottom flask equipped with a condenser, thermometer and magnetic stirrer. To the solution was added 32.8 grams (0.21 mole) of allyl levulinate and 17.6 grams (0.22 mole) of 50% sodium hydroxide. The mixture was stirred and heated to reflux for 4 hours. It was allowed to cool to 70° C. and the layers separated. Upon further cooling, the organic layer was dissolved in pentane and the pentane solution dried over anhydrous sodium sulfate, filtered and the pentane stripped off on a rotating evaporator under reduced pressure. The resulting yellow liquid weighed 46.0 grams (76% crude yield). The infrared spectrum of the product had a strong band at 1720 cm$^{-1}$ (ester carbonyl band) and a strong carbon-oxygen band at 1160 cm$^{-1}$ indicating the allyl ester group was still intact. There was a weak sharp band at 1640 cm$^{-1}$ (C=N) and another weak sharp band at 1600 cm$^{-1}$ (phenyl absorption) indicating that the t-cumylhydrazone had formed.

(C) Preparation of Allyl 4-t-Cumylazo-4-chlorovalerate

To a 500 ml 3-neck round bottom flask, equipped with a mechanical stirrer, thermometer, condenser and chlorine inlet tube, was added 40.2 grams (0.14 mole) of allyl levulinate t-cumylhydrazone, 200 mls of pentane and 15.2 grams (0.15 mole) of triethylamine. The solution was cooled to 5° C. and with good agitation 9.95 grams (0.14 mole) of chlorine was slowly added over 20 minutes while holding the temperature between 5° and 15° C. After the addition was complete, the mixture was stirred for 10 minutes at 10° C. and filtered. The triethylamine hydrochloride filter cake was rinsed with pentane and pulled semi-dry by vacuum. The filtrates were combined and the pentane was stripped off on a rotary evaporator under reduced pressure. The resulting yellow liquid weighed 44 grams (97.4% crude yield). The infrared spectrum of the product contained a strong band at 1720 cm$^{-1}$ (ester carbonyl band) and a strong carbon-oxygen band at 1160 cm$^{-1}$ indicating the allyl ester group was still intact.

(D) Preparation of Allyl 4-t-Cumylazo-4-cyanovalerate

To a 100 ml 3-neck round bottom flask, equipped with magnetic stirrer, thermometer and addition funnel, was added 2.94 grams (0.06 mole) of sodium cyanide and 50 mls of 75% aqueous methanol. The mixture was stirred at room temperature until the sodium cyanide dissolved. The solution was cooled to 10° C. and 13.0 grams (0.04 mole) of allyl 4-t-cumylazo-4-chlorovalerate were added dropwise over twenty minutes while holding the temperature at 10°-15° C. After the addition was complete, the mixture was stirred for 90 minutes at 15° C., poured into 150 ml of water and the organic layer taken up in 100 mls of pentane. The pentane layer was separated, washed with 5% HCl, concentrated HCl, water and saturated sodium bicarbonate. The solution was dried over anhydrous sodium sulfate, filtered and the pentane stripped off on a rotary evaporator under reduced pressure. The resulting yellow liquid weighed 9.0 grams (72% crude yield). The infrared spectrum of the product contained a strong band at 1720 cm$^{-1}$ (ester carbonyl band) and a strong carbon-oxygen band at 1160 cm$^{-1}$ indicating the allyl ester group was still intact. The compound also had a weak cyano band at 2200 cm$^{-1}$ indicating the chlorine substituent had been replaced by the cyano substituent.

EXAMPLE 35

Preparation of Allyl 4-t-Cumylazo-4-allyloxyvalerate

To a 100 ml 3-neck round bottom flask, equipped with a magnetic stirrer, thermometer and addition funnel, was added 60 mls of allyl alcohol and 3.29 grams (0.05 mole) of 85% potassium hydroxide. The mixture was stirred at room temperature until the potassium hydroxide dissolved. The solution was cooled at 15° C. and 13.0 grams (0.04 mole) of allyl 4-t-cumylazo-4-chlorovalerate was added over 15 minutes while holding the temperature at 15°-20° C. After the addition was complete, the mixture was stirred for 60 minutes at room temperature, poured into 200 ml of water and the organic layer taken up in 100 mls of pentane. The pentane layer was separated, washed with water, 0.1 N HCl, water and saturated sodium bicarbonate. The pentane solution was dried over anhydrous sodium sulfate, filtered and the pentane stripped off on a rotating evaporator under reduced pressure. The resulting yellow liquid weighed 5.0 grams (36.4% crude yield). The infrared spectrum of the product contained a strong band at 1720 cm$^{-1}$ (ester carbonyl band) and a strong carbon-oxygen band at 1160 cm$^{-1}$ indicating the allyl ester group was still intact. There was another strong carbon-oxygen band at 1110 cm$^{-1}$ (allyl ether band) and the band at 1640 cm$^{-1}$ (unsaturation) had doubled in intensity indicating the chlorine substituent had been replaced by the allyloxy substituent.

EXAMPLE 36

Preparation of 4-t-Butylazo-4-Substituted-pentanols

A. Preparation of 3-Acetylpropyl Acetate

To a 1 liter 3-neck round bottom flask equipped with a stirrer, thermometer, condenser and addition funnel, was added 102 grams (1 mole) of 3-acetylpropanol, 125 mls of pyridine and 600 mls of methylene chloride. With ice cooling and good agitation, 78.5 grams (1 mole) of acetyl chloride was added slowly from the addition funnel while holding the temperature at 25° C. or below. Pyridine hydrochloride began coming out of solution about ⅓ of the way through the addition. After the addition was complete, the reaction mixture was stirred an additional 15 minutes at 20°–25° C. and then warmed to 40° C. and stirred an hour at 40° C. Then 150 mls of water were added to dissolve the pyridine hydrochloride and the aqueous layer was separated. The organic layer was washed twice with 200 mls of 10% HCl, once with water and saturated sodium bicarbonate solution. The organic layer was dried over anhydrous sodium sulfate, filtered and the methylene chloride stripped off on a rotary evaporator under reduced pressure. The light yellow liquid weighed 104 grams (72% crude yield). The infrared spectrum of the product contained two strong carbonyl bands at 1720 cm$^{-1}$ and 1745 cm$^{-1}$ and there was no OH band.

B. Preparation of the t-Butylhydrazone of 3-Acetylpropyl Acetate

To a 1500 ml 3-neck round bottom flask, equipped with a reflux condenser, thermometer, magnetic stirrer and immersed in an oil bath, was added 871.2 grams (0.86 mole) of a 12.3% solution of t-butylhydrazine hydrochloride, 104 grams (0.74 mole) of 3--acetylpropyl acetate and 73 grams (0.91 mole) of 50% sodium hydroxide. The mixture was stirred, heated to reflux in the oil bath and refluxed for 5½ hour at 98° C.±2°. The reaction mixture was cooled to 40° C. and the organic layer separated. The organic layer was cooled to room temperature, taken up in pentane, dried over anhydrous sodium sulfate, filtered and the pentane stripped off on a rotary evaporator under reduced pressure. The resulting yellow liquid weighed 126 grams (81% crude yield). The infrared spectrum contained one carbonyl absorption band at 1740 cm$^{-1}$ and a C≡N absorption band at 1640 cm$^{-1}$ and a strong carbon-oxygen band at 1240 cm$^{-1}$ indicating that the t-butylhydrazine reacted well with the ketone carbonyl group to form the t-butylhydrazone and did not react with the ester group.

C. Preparation of 4-t-Butylazo-4-chloropentyl Acetate

To a 1 liter 3-neck round bottom flask equipped with a mechanical stirrer, thermometer, chlorine inlet tube and condenser, was added 107.1 grams (0.5 mole) of 3-acetylpropyl acetate t-butylhydrazone, 600 ml of pentane and 52.7 grams (0.52 mole) of triethylamine. The resulting solution was cooled to 5° C. and with rapid stirring 35.5 grams (0.5 mole) of chlorine was slowly added over 25 minutes while holding the temperature between 5° and 10° C. with an ice bath. After the addition was complete, the mixture was stirred an additional 5 minutes at 5° to 10° C. before adding 204 grams (0.51 mole) of 10% sodium hydroxide. The mixture was stirred until all the triethylamine hydrochloride had been neutralized. The aqueous layer was separated and the pentane solution was washed with water and saturated sodium bicarbonate, dried over anhydrous sodium sulfate, filtered and the pentane and triethylamine stripped off on a rotary evaporator under reduced pressure. The resulting yellow liquid weighed 131 grams and still contained some triethylamine. The infrared spectrum of the product contained a strong carbonyl absorption at 1730 cm$^{-1}$ and a strong carbon-oxygen band at 1230 cm$^{-1}$ indicating that the acetate group was still intact. There was a weak carbon-chlorine band at 850 cm$^{-1}$ and C≡N absorption at 1640 cm$^{-1}$ was missing.

D. Preparation of 4-t-Butylazo-4-cyanopentanol

To a 200 ml 3-neck bottom flask equipped with a magnetic stirrer, thermometer and addition funnel was added 10.3 grams (0.21 mole) of sodium cyanide and 80 mls of 75% aqueous methanol. The mixture was stirred at room temperature until the sodium cyanide dissolved. The solution was cooled to 10° C. and 49.7 grams (0.2 mole) of 4-t-butylazo-4-chloropentyl acetate was added dropwise over 20 minutes while holding the temperature at 10° to 15° C. with a cold water bath. After the addition was complete, the mixture was stirred an additional hour at room temperature before adding 13.2 grams (0.2 mole) of 85% potassium hydroxide. The resulting mixture was stirred an additional ½ hour at room temperature to complete the saponification of the acetate group. The reaction mixture was poured into 200 ml of water and the organic layer taken up in 100 ml pentane. The pentane solution was washed with water, 10% HCl, water and saturated sodium bicarbonate solution. The pentane solution was dried over anhydrous sodium sulfate, filtered and the pentane stripped off on a rotary evaporator under reduced pressure. The resulting light orange liquid weighed 11.0 grams (28% crude yield). The infrared spectrum of the product contained a sharp weak cyano band at 2200 cm$^{-1}$ and a very strong broad hydroxyl peak at 3300 cm$^{-1}$. The carbonyl band at 1730–1740 cm$^{-1}$ and the carbon-oxygen band at 1230–1240 cm$^{-1}$ were missing, indicating that the acetoxy group had been saponified.

E. Preparation of 4-t-Butylazo-4-methoxypentanol

To a 250 ml 3-neck round bottom flask equipped with a magnetic stirrer, thermometer, condenser and addition funnel was added 13.2 grams (0.2 mole) of 85% potassium hydroxide pellets and 130 mls of methanol. The mixture was stirred at approximately 30° C. until the pellets dissolved. The resulting solution was cooled at 10° C. and with rapid stirring 24.9 grams (0.1 mole) of 4-t-butylazo-4-chloropentyl acetate were added over 20 minutes while holding the temperature at 10°–15° C. After the addition was complete, the mixture was stirred for 3 hours at room temperature, poured into 300 mls of water and the organic layer taken up in 100 mls of methylene chloride. The aqueous layer was separated and discarded and the methylene chloride was washed with water, 10% HCl, water and saturated sodium bicarbonate solution. The methylene chloride solution was dried over anhydrous sodium sulfate, filtered and the methylene chloride stripped off on a rotary evaporator under reduced pressure. The resulting light orange liquid weighed 12.5 grams (62% crude yield). The infrared spectrum of the product contained a very broad strong OH band centered at 3400 cm$^{-1}$ and no carbonyl band. There was a strong carbon-oxygen band at 1180–1220 cm$^{-1}$.

F. Preparation of 4-t-Butylazo-4-(p-t-butylthiophenoxy) pentanol

To a 250 ml 3-neck round bottom flask equipped with a magnetic stirrer, thermometer, condenser and addition funnel was added 6.6 grams (0.1 mole) of 85% potassium hydroxide pellets and 130 mls of methanol.

The mixture was stirred at 30° C. until the pellets dissolved. The resulting solution was cooled to 15° C. and with rapid stirring 16.6 grams (0.1 mole) of para-t-butyl-thiophenol were added while holding the temperature at 15° to 20° C. The mixture was stirred an additional 15 minutes at 15° C. and then 24.9 grams (0.1 mole) of 4-t-butylazo-4-chloropentyl acetate were added over 20 minutes while holding the temperature at 15° to 20° C. After the addition was complete, the mixture was stirred an additional hour at room temperature and then an additional 6.6 grams (0.1 mole) of 85% potassium hydroxide was added (to saponify the acetyl group). The mixture was stirred an additional 1 hour at room temperature, poured into 300 mls of water and the organic layer taken up in 100 mls of methylene chloride. The methylene chloride layer was separated, washed with 50 ml portions of water, 10% HCl, water and saturated sodium bicarbonate solution, dried over anhydrous sodium sulfate, filtered and the methylene chloride stripped off on a rotary evaporator under reduced pressure. The resulting light orange liquid weighed 28 grams (83.5% crude yield). The infrared spectrum of the product contained a very broad strong OH band centered at 3350–3400 cm$^{-1}$ and there was no carbonyl band.

EXAMPLES 37–39

Preparation of Acrylate Esters of 4-t-Butylazo-4-substituted-pentanols

The 4-t-butylazo-4-substituted pentanols prepared in Example 36 D–F were esterified with acryloyl chloride in methylene chloride using pyridine as an acid acceptor.

To a 100 ml 4-neck roundbottom flask equipped with a magnetic stirrer, thermometer, condenser and addition funnel, was added 0.025 mole of the 4-t-butylazo-4-substituted-pentanol, 5.0 grams pyridine and 25 mls of methylene chloride. With stirring, 2.7 grams (0.03 mole) of acryloyl chloride were added dropwise from the addition funnel over 10 minutes while holding the temperature at 25°–30° C. The reaction mixture was then warmed to 40° C. and stirred 3 hours at 40° C. ±2° C. At the end of the reaction period, 50 mls of water were added to dissolve the pyridine hydrochloride. The methylene chloride layer was separated and washed with 50 ml portions of 10% HCl, water and saturated sodium bicarbonate solution. The methylene chloride solution was dried over anhydrous sodium sulfate, filtered and the methylene chloride stripped off on a rotary evaporator under reduced pressure. The resulting liquid was weighted and the crude percent yield determined. The infrared spectra of the products contained strong sharp carbonyl bands at 1720 cm$^{-1}$ and strong carbon-oxygen bands at 1180–1200 cm$^{-1}$. The yields of the individual compounds are given in the following table.

| Example # | Compound | Crude % Yield |
|---|---|---|
| 37 | 4-t-Butylazo-4-cyanopentyl Acrylate | 92 |
| 38 | 4-t-Butylazo-4-methoxypentyl Acrylate | 62 |
| 39 | 4-t-Butylazo-4-(p-t-butylthiophenoxy)-pentyl Acrylate | 45 |

EXAMPLES 40–42

Preparation of n-Butyl 4-t-Butylazo-4-substituted-pentyl Maleates

A. Preparation of the Mono Butyl Ester Mono Acid Chloride of Maleic Acid

To a 100 ml 4-neck round bottom flask equipped with a thermometer, water-cooled condenser and magnetic stirrer, was added 23.8 grams (0.2 mole) of thionyl chloride. The thionyl chloride was stirred and 17.2 grams (0.1 mole) of monobutyl maleate were added dropwise over 25 minutes while holding the temperature at 25° to 30° C. The mixture was then stirred 3 hours at 35°–37° C. and 1 hour at 40°–45° C. The contents of the flask were then stripped of HCl, SO$_2$ and the excess thionyl chloride under vacuum for 2 hours at 60°–70° C. The stripped liquid weighed 20.0 grams (theory=19 grams). The infrared spectrum of the product contained a strong carbonyl band at 1780 cm$^{-1}$ (acid chloride) and a strong carbonyl band at 1720–1740 cm$^{-1}$ (ester) and there was only a trace of the hydroxyl band at 3280 cm$^{-1}$.

B. Preparation of n-Butyl 4-t-Butylazo-4-substituted-pentyl Maleates

The 4-t-butylazo-4-substituted pentanols prepared in Example 36 D–F were esterified with the acid chloride prepared in part A using pyridine as an acid acceptor. To a 100 ml 4-neck round bottom flask equipped with a magnetic stirrer, thermometer, condenser and addition funnel, was added 0.025 mole of the 4-t-butylazo-4-substituted-pentanol, 5.0 grams of pyridine and 35 mls of methylene chloride. With good stirring, 5.7 grams (0.03 mole) of the mono butyl ester mono acid chloride of maleic acid were added dropwise from the addition funnel over 10 minutes while holding the temperature at 25°–30° C. The reaction mixture was warmed to 40° C. and stirred for 1½ hours. At the end of the reaction period, 50 mls of water were added to dissolve the pyridine hydrochloride. The methylene chloride layer was separated and washed with 50 ml portions of 10% HCl, water and saturated sodium bicarbonate solution. The methylene chloride solution was dried over anhydrous sodium sulfate, filtered and the methylene chloride stripped off on a rotary evaporator under reduced pressure. The resulting liquid was weighed and the crude percent yield determined. The infrared spectra of the products contained strong carbonyl bands at 1710–1740 cm$^{-1}$, weak unsaturation bands at 1160 cm$^{-1}$. The hydroxyl bands of the starting alcohols at 3300 cm$^{-1}$ were missing.

The crude percent yields of the individual compounds are given in the following table.

| Example # | Compound | Crude % Yield |
|---|---|---|
| 40 | n-Butyl 4-t-Butylazo-4-cyanopentyl Maleate | 99% |
| 41 | n-Butyl 4-t-Butylazo-4-methoxypentyl Maleate | 86% |
| 42 | n-Butyl 4-t-Butylazo-4-(p-t-butylthiophenoxy)-pentyl Maleate | 99% |

What is claimed:
1. A compound of the formula

$$(R'')_3C-N=N-\underset{X}{\overset{R_1}{\underset{|}{C}}}-R_2$$

wherein:
(a) R''s are independently selected from alkyl of 1 to 8 carbons, aralkyl of 7 to 12 carbons, or aryl of 6 to 14 carbons, with the proviso that only one R'' may be aryl, the R''s can also be joined to form a cyclo, bicyclo or tricyclo of 3 to 12 carbons;
(b) $R_1$ and $R_2$ are independently selected from alkyl of 1 to 8 carbons, cycloalkyl of 3 to 12 carbons, aralkyl of 7 to 12 carbons, or a ring substituted cycloalkyl of 5 to 6 carbons wherein the ring substituent is one or more of oxygen, nitrogen or sulfur, $R_1$ and $R_2$ can be joined to form an alkylene diradical of 3 to 11 carbons, $R_1$ can also be an aryl of 6 to 14 carbons;
(c) X is selected from $-CN$, $-\overset{O}{\underset{\|}{C}}-NH_2$, $-\overset{O}{\underset{\|}{C}}OR_3$, $-\overset{H}{\underset{\|}{\overset{N}{C}}}-NH_2$, $-\overset{H}{\underset{\|}{\overset{N}{C}}}OR_4$, $-O\overset{O}{\underset{\|}{C}}H$, $-Y-\overset{Y}{\underset{\|}{C}}-Y-R_3$, $-Y-\overset{Y}{\underset{\|}{C}}-R_3$, $-Y-R_3$, $-N_3$, $-OOCR_3$, $-OOH$, $-OOC(R'')_3$, $-N\begin{matrix}\overset{O}{\underset{\|}{C}}-R_5\\ \underset{\|}{C}-R'_5\\O\end{matrix}$ or $-N\begin{matrix}\overset{O}{\underset{\|}{C}}\\ \diagdown\\\diagup O\\N=C-R_6\end{matrix}$;

(d) Y is selected from oxygen or sulfur.
(e) $R_3$ is selected from alkyl of 1 to 8 carbons, cycloalkyl of 3 to 12 carbons or aryl of 6 to 14 carbons;
(f) $R_4$ is selected from alkyl of 1 to 6 carbons;
(g) $R_5$ and $R'_5$ are independently selected from alkyl of 1 to 8 carbons or aryl of 6 to 14 carbons, $R_5$ and $R'_5$ can be joined to form an alkylene diradical of 1 to 8 carbons or an arylene diradical of 6 to 14 carbons;
(h) $R_6$ is selected from hydrogen, alkyl of 1 to 8 carbons, cycloalkyl of 3 to 12 carbons or aryl of 6 to 14 carbons;
(i) one of $R_1$, $R_2$, $R_3$, $R_4$, $R_5$, $R_6$ or R'' must be substituted with $\underset{H}{\overset{R_8}{\diagdown}}C=\underset{|}{\overset{R_7}{C}}-A-$ (j) $R_7$ is selected from hydrogen, alkyl of 1 to 6 carbons or Cl—;
(k) $R_8$ is selected from hydrogen or $R_9O\overset{O}{\underset{\|}{C}}-$;

(l) $R_9$ is selected from H or alkyl of 1 to 6 carbons;
(m) when $R_8$ is hydrogen, A is selected from $-\underset{|}{\overset{R_9}{CH}}-Z-$, $-\overset{Y}{\underset{\|}{C}}-Y-R_{10}'-$ or $-R_{11}-R_{10}'-$;

(n) when $R_7$ and $R_8$ are both hydrogen, A is selected from $-Y-R_{10}'-$, $-Y-\overset{Y}{\underset{\|}{C}}-R_{10}'-$, $-Y-\overset{Y}{\underset{\|}{C}}-Y-R_{10}'-$, or $-\overset{O}{\underset{\|}{C}}-R_{10}'-$;

(o) when $R_8$ is $R_9O\overset{O}{\underset{\|}{C}}-$, $R_7$ is hydrogen and A is $-\overset{O}{\underset{\|}{C}}OR_{10}'-$ (p) Z is selected from $YR_{10}'-$, $-Y-\overset{Y}{\underset{\|}{C}}-R_{10}'-$, $-Y-\overset{Y}{\underset{\|}{C}}-YR_{10}'-$, $-Y-\overset{H}{\underset{\|}{\overset{N}{C}}}-R_{10}'-$ or $-\overset{O}{\underset{\|}{C}}R_{10}'-$;

(q) $R'_{10}$ is selected from a covalent or $-R_{10}D-$;
(r) $R_{10}$ is selected from alkylene of 1 to 8 carbons;
(s) D is selected from $-Y-$, $-Y-\overset{Y}{\underset{\|}{C}}-$, $-Y-\overset{Y}{\underset{\|}{C}}-Y-$, $-Y-\overset{H}{\underset{\|}{\overset{N}{C}}}-$, $-\overset{H}{\underset{\|}{N}}-\overset{Y}{\underset{\|}{C}}-$ or covalent bond; and
(t) $R_{11}$ is selected from aryl of 6 to 14 carbons, pyridine, carbazole, pyrrolidone, piperidone or caprolactam.

2. The compound of claim 1 wherein R''s are $-CH_3$, $R_1$ is $-CH_3$, $R_2$ is $-CH_2CH_2\overset{O}{\underset{\|}{C}}OCH_2CH=CH_2$, and X is $-CN$, $Cl-$, $N_3$, $-OOC(CH_3)_3$, or $-SC_6H_5$.

3. The compound of claim 1 wherein R''s are $-CH_3$, $R_1$ is $-CH_3$, $R_2$ is $-CH_2CH_2\overset{O}{\underset{\|}{C}}OCH_2CH_2O\overset{O}{\underset{\|}{C}}-\underset{\underset{CH_3}{|}}{C}=CH_2$, and X is $-CN$.

4. The compound of claim 1 wherein R''s are $-C_2H_5$, $-CH_3$ and $-CH_3$, $R_1$ is $-CH_3$, $R_2$ is $-CH_2CH_2COCH_2CH=CH_2$ and X is $-CN$, $CH_3CO-$,
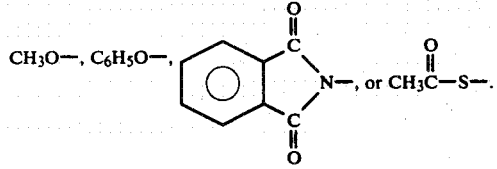
$CH_3O-$, $C_6H_5O-$, [phthalimide-N-], or $CH_3C(O)-S-$.
5. The compound of claim 1 wherein R"s are $-C_6H_5$, $-CH_3$, and $-CH_3$, $R_1$ is $-CH_3$, $R_2$ is
$-CH_2CH_2COCH_2CH=CH_2$
and X is $-CN$, or $-OCH_2CH=CH_2$.
6. The compound of claim 1 wherein R"s are $-CH_3$, $R_1$ is $-CH_3$, X is $-CN$ and $R_2$ is
$+CH_2\!\!+_3 OCCH=CHCOC_4H_9$ or $+CH_2\!\!+_3 OCCH=CH_2$.
* * * * *